Figure 1:
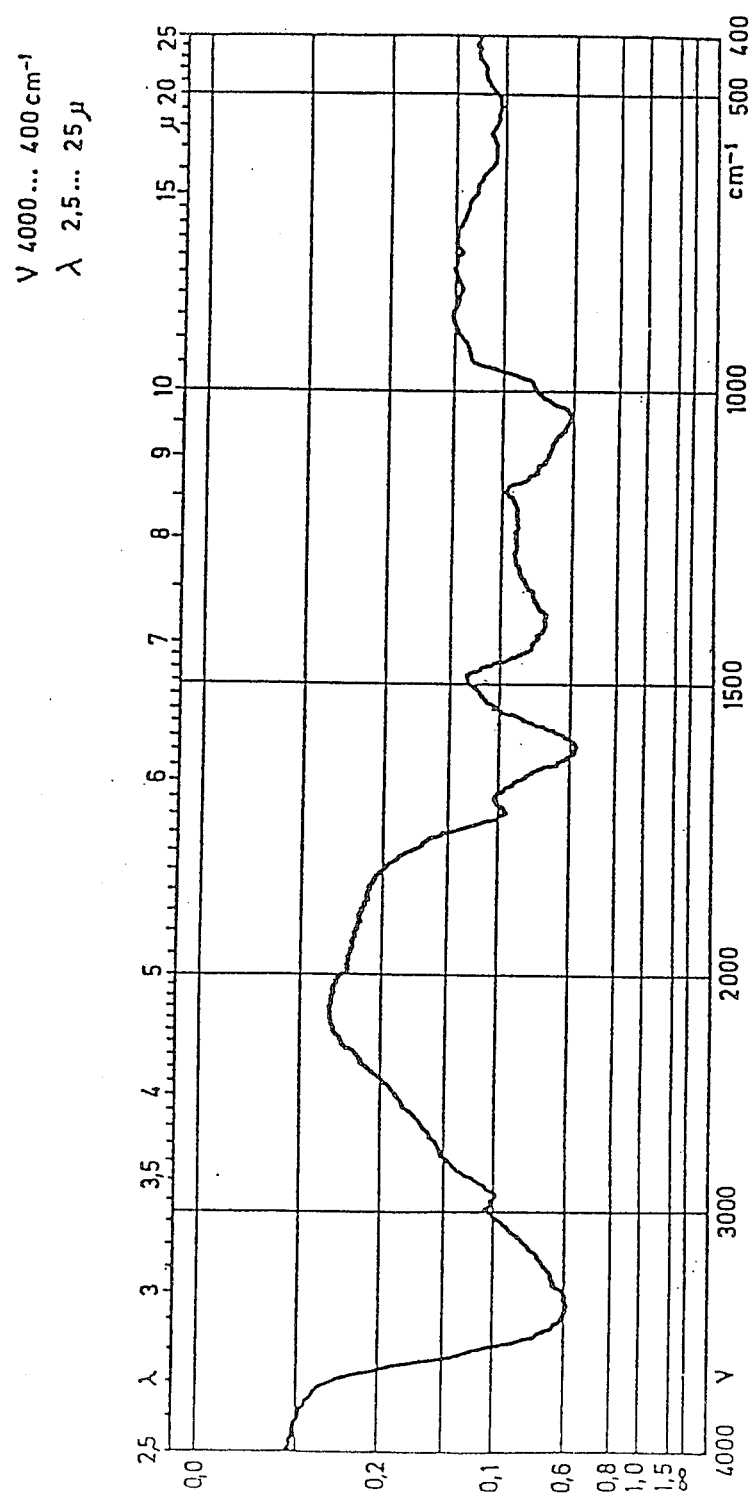

United States Patent [19]

Hoffmann

[11] 4,383,833

[45] May 17, 1983

[54] NATURAL EDIBLE DYE PREPARATION FROM BEAN HUSKS GIVING RED SHADES

[75] Inventor: Paul Hoffmann, Holzminden, Fed. Rep. of Germany

[73] Assignee: Dragoco Gerberding und Co. GmbH, Holzminden, Fed. Rep. of Germany

[21] Appl. No.: 355,758

[22] PCT Filed: Jun. 11, 1981

[86] PCT No.: PCT/DE81/00089

§ 371 Date: Feb. 19, 1982

§ 102(e) Date: Feb. 19, 1982

[87] PCT Pub. No.: WO82/00035

PCT Pub. Date: Jan. 7, 1982

[30] Foreign Application Priority Data

Jun. 20, 1980 [DE] Fed. Rep. of Germany ....... 3023178

[51] Int. Cl.$^3$ .............................................. C09B 61/00
[52] U.S. Cl. ............................................ 8/438; 8/436; 8/499; 8/919; 426/46
[58] Field of Search .................... 8/438, 436, 499; 426/46

[56] References Cited

U.S. PATENT DOCUMENTS

| 4,156,077 | 5/1979 | Pifferi | 8/438 |
| 4,204,043 | 5/1980 | Schultz | 8/438 |
| 4,331,765 | 5/1982 | Sakaguchi | 435/267 |
| 4,333,955 | 6/1982 | Murata et al. | 426/46 |

FOREIGN PATENT DOCUMENTS 761567 7/1971 Belgium .
48-17825 6/1973 Japan .

*Primary Examiner*—A. Lionel Clingman
*Attorney, Agent, or Firm*—Browdy and Neimark

[57] ABSTRACT

A natural, edible dye, characterized by particular infrared and ultraviolet spectra and a method for its production, in which cell walls of the skins of colored beans of the genus Phaseolus, such as black beans, are destroyed, the released dye is extracted with water or an aqueous solution of a weak organic acid after weak acidulation, the obtained extract is separated from the skin residues, and the solution is concentrated and dried. The dye is used, in particular, for coloring foodstuffs and snack foods, beverages, pharmaceutical and cosmetic products, and for coloring textiles, paper and leather.

11 Claims, 2 Drawing Figures

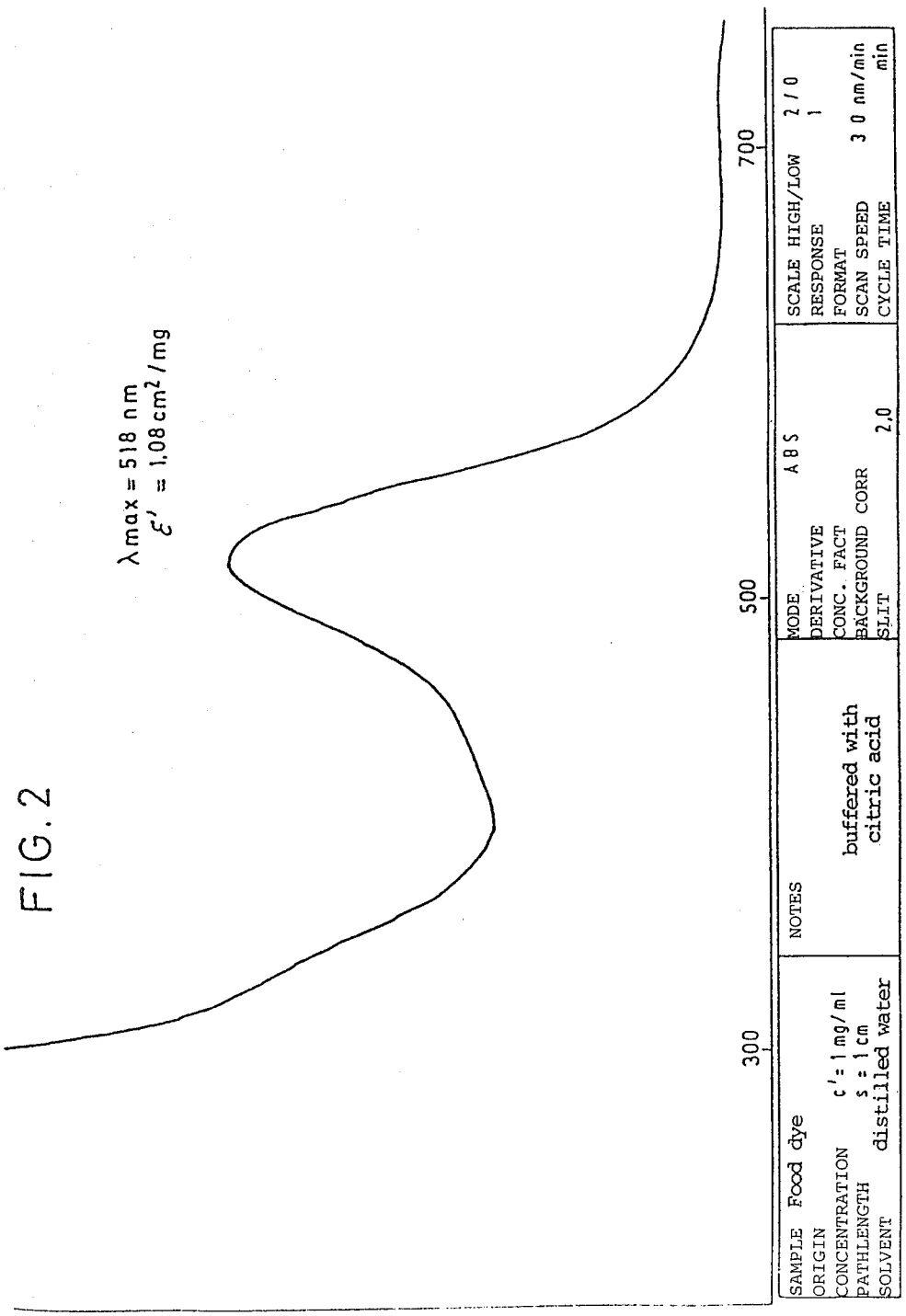

NATURAL EDIBLE DYE PREPARATION FROM BEAN HUSKS GIVING RED SHADES

At the present time, synthetic dyes are predominantly used for foodstuffs, snack foods, beverages, and pharmaceutical and cosmetic products. Since some of these dyes are physiologically objectionable and since the consumer has become more aware of the environment, the trend is toward using natural dyes. This trend is reinforced by laws and legal opinion in the field of foodstuff law in all the countries of the world.

Where natural dyes from flowers or fruits, such as hibiscus flowers or elderberries, are already being used for products such as those named above, the dyes are obtained by extraction methods and have the disadvantage that they are not sufficiently stable under the effect of heat and light and that they can be standardized only with great difficulty.

Surprisingly, it has now been discovered that the dye in the infrared and ultraviolet spectra shown in FIGS. 1 and 2 respectively and obtainable from natural raw materials eliminates the above disadvantages. Experiments have shown that products treated with this dye exhibit no changes in color at all, even after being stored in daylight and at room temperature for one year. Even higher temperatures such as those in the tropics do not affect the color quality. When diluted to the extent which is normal in this field, the dye is a strong red, and colorings from pink to deep dark-bluish red can be attained with this dye, depending on the concentration, as shown in the following table:

TABLE 1

Coloration of 0.1% solutions of the dye in $H_2O$ (dye extracted with citric acid)

pH 1.0: attractive, strong red without lavender tinge (acidulated with HCl)
pH 3.0: red with slight lavender tinge
pH 4.0: red with slight lavender tinge, but more pronounced than at pH 3.0
pH 5.6: red with lavender tinge, the color of eggplant
pH 7.0: brownish-green (adjusted with $NH_4OH$)
pH 9.0: green
pH 12.0: green with yellow tinge (adjusted with NaOH)

After being made alkaline and then reacidulated, the color intensity fades and changes to orange (pH 4.0).

A 10% dye solution is a pronounced eggplant color (pH 5.5).

For dyeing purposes in the field of foodstuffs, the following concentrations are suitable:
pale pink: 0.05% solution, pH 4.5
strong red: 0.35% solution, pH 4.5
deep red: 0.55% solution, pH 4.5

A solution concentrated to 50 Brix and then spray-dried produces a powder of almost black-violet color.

It is worthy of mention that the dye solution can also be concentrated at normal atmospheric pressure and 100° C., without destroying the dye.

The method for producing the dye begins with colored beans of the genus Phaseolus, especially the black-colored cultivated forms of common beans (*Phaseolus vulgaris*), which are one of the basic foods of the indigenous population in South America. This raw material is substantially less expensive than other natural dye sources or the raw material for synthetic dyes. The skins of all the colored varieties of the genus, Phaseolus, can be used as raw material. Besides the *Phaseolus vulgaris* already mentioned, scarlet runner beans (*Phaseolus coccineus*) and *Phaseolus caracalla* could be especially named.

The method includes the following basic steps:

(a) The skins of the above-noted black beans, either uncooked or efficaciously briefly soaked, or a powder of these skins is boiled for some time with enough slightly acidic water, preferably the aqueous solution of a hydroxycarboxylic acid, so that an easily stirrable suspension results. After 10 to 15 minutes' boiling, the pH value should be at approximately 5 to 5.5.

(b) After being cooled to the temperature which is efficacious for the following method step, the cell walls of the bean skins are at least partially destroyed in order to release the dye. The cell wall destruction is effected in a manner known per se by enzymatic decomposition, grinding at low temperatures, possibly with the addition of dry ice and/or fine aluminum oxide, or by autoclaving under elevated pressure and increased temperature, or by high-pressure extraction with super-critical gases such as $CO_2$, or by liquid-liquid extraction with suitable solvents, such as methanol.

(c) The resultant suspension is again brought to a pH value of approximately 4 to 4.5 by adding some acid as required. It is then advantageous to boil up the suspension, which is appropriate in any event in enzymatic decomposition in order to destroy the enzyme but which also serves to release the maximum amount of dye from the cells.

(d) The resultant suspension is separated into skin residues on the one hand and the dye solution on the other; this may be effected by filtering, or centrifuging and the like. Finally, (e) The dye solution is concentrated in a manner known per se, to a state of dryness if needed; this may be effected by means of concentration, especially in a vacuum, or by spray-drying.

Method step (a) may also be performed using whole beans, which have been boiled and/or crushed as needed. The product is not fundamentally changed thereby. In the case of enzymatic cell wall decomposition, as in decomposition by means of autoclaving, it is preferably the cell walls of the bean skins which are affected. However, the greater quantity which must be processed efficaciously requires a second boiling in step (a), making the method more expensive. In the case of cell destruction by means of grinding whole beans, naturally the concentration of the dye in the complete mixture is very much lower, and the boiling and extraction steps must be repeated several times, all of which results in a less elegant method. Since mechanical peeling machines for legumes are known, and the bean kernels produced by peeling are available for other uses such as pureed beans, the usage of bean skins as raw material is greatly preferred. In the peeling process, the top-most layer of the beans, just beneath the skin, should also be removed, because it contains dye as well. Conventional peeling machines remove approximately 10% of the mass of the kernel along with the skin. The powdered skin produced as a residue, when peeling black beans for white bean puree, is also very suitable as a raw material. The vertical polishing machine for rice, cereals and legumes produced by the Bühler-Miag company and known as type DSRD has endured the test of time as a peeling machine.

For acidulation in steps (a) and (c), relatively weak organic acids have proved particularly suitable; hydroxycarboxylic acids and especially citric acid are preferred. Ascorbic acid can also be mentioned as being particularly suitable.

The critical step in the present method is the destruction of the cell walls of the bean skins to an extent which permits the passage of the dye through the cell walls. The usage of acid amylase in this method step has the further advantage that the cell walls surrounded by starch particles are easily and rapidly broken open sufficiently, and so the dye contained in the cell can be isolated to obtain a particularly high yield.

The dye produced by this method can be put on the market either in the form of a solution or in the form of some dry substance desired by the user and produced by known methods, for instance being concentrated to about 60% of it mass, or being pulverized.

The intensity of coloring attained can be varied in a simple manner for all the products to be dyed, by changing the quantity of dye or, as shown in Table I supra, by varying the pH.

The constitution of the dye is defined by the attached spectra. The essential physical-chemical properties, particularly resistance to heat and light, distinguish the dye from the known anthocyanines, so that it must be presumed that this is a specialized anthrocyanine dye complex which is modified and stabilized by means of the specialized manner in which it is produced.

The following examples explain the invention. The black beans used as raw material are beans of the genus *Phaseolus vulgaris*.

EXAMPLE 1

This example shows the production of the dye from the skins of black beans.

1000 g of black beans are mechanically peeled, obtaining 250 g of skins which are required for the rest of the method. The remaining bean puree is separated out and is available for other uses. In the peeling process, the topmost, markedly colored layer of the bean kernel itself is also peeled off. A conventional laboratory machine, available on the market and of the kind known for peeling legumes, is used.

The 250 g of skins obtained are boiled for 10 minutes with a mixture of 2 liters water and 0.5 g pulverized, crystallized citric acid, raising the pH value to from 5 to 5.5.

The resultant mixture is cooled down to a temperature from 53° to 56° C. in order to provide the optimal pH and temperature values for the subsequent enzyme treatment.

While maintaining the temperature, 0.5 g of acid amylase (from the company, Röhm Pharma GmbH) is added to the mixture, the incubation time being 30 minutes.

Then 14 g citric acid of 50% strength is added to the mixture and the entire amount is then boiled for 5 minutes in order to stop the enzyme activity. The pH value after the new addition of acid is approximately 4.

The suspension thus obtained is then filtrated through a hair sieve, and the solution obtained is concentrated in a vacuum (40 torr) or spray-dried.

In a 0.1% aqueous solution (pH 4), the dye obtained has a pronounced red coloring with a slight tinge of lavender.

The spray-dried dye is black-violet in color.

EXAMPLE 2

Example 1 was repeated, this time using the powdered skins produced as a byproduct in peeling beans for making white bean flour.

Using 250 g of powdered skins, the process was identical to that of example 1, except that the 250 g of powdered skins were boiled for 10 minutes with a mixture of 1 liter water and 0.5 g pulverized, crystallized citric acid and then further processed as described above for example 1. The same dye was produced. Virtually all the dye is removed from the skins if the breakdown of the cell walls is sufficiently intensive. When citric acid is used, the yield is approximately 2 to 2.5% of the weight of the skins originally used.

A repetition of example 1 using ascorbic acid instead of citric acid in the same quantities produced a yield of from 1.8 to 2.0%.

EXAMPLE 3

2000 g of black beans are peeled mechanically, obtaining 500 g of skins required for the rest of the method. The residue of bean puree is separated out and is available for other uses. In the peeling process, the topmost, markedly colored layer of the bean kernel itself is also peeled away. A conventional laboratory machine, available on the market, such as is known for peeling legumes is used.

The 500 g of skins obtained are mixed with 2.5 liters water, and this aqueous suspension is treated with a hydroxycarboxylic acid, adjusting the pH value to 4. The autoclaving procedure is performed over a period of one hour at a pressure of 150 bar and a temperature of 80° C. Further processing is performed as in example 1. The yield is approximately 2%. For the oxylic acid, citric acid was used in one experiment, ascorbic acid in a second and tartaric acid in a third. Practically the same results were obtained each time.

The following examples illustrate the usage of the dye:

| | I - Hard Candy |
|---|---|
| 8.58 | l water |
| 26.0 | kg sugar |
| 8.0 | kg glucose (43–45° Baumé) |
| 0.375 | kg citric acid |
| 0.037 | kg flavoring |
| 0.400 | kg food coloring (5% dye solution in water) |
| 43.40 | |
| | II - Sherbet |
| 2.5 | kg binder mixture |
| 30.0 | kg granulated sugar |
| 5.0 | kg starch syrup 43° Baumé |
| 61.615 | kg water |
| 0.035 | kg citric acid |
| 0.850 | kg dye solution (3% in water) |
| 100.000 | kg mixture |
| | III - Lemonade Beverage |
| 13.32 | l sugar syrup, 65% |
| 0.058 | l benzoic acid, 30% |
| 0.072 | l citric acid, 50% |
| 0.100 | kg flavoring |
| 0.850 | l dye solution, 2.5% by weight in water |
| IV - Bitters | Aperitif (alcoholic), of the "Campari" type |
| 29.5 | l alcohol, 90% by volume |
| 43.1 | l water |
| 22 | l sugar solution, 65% |
| 3.0 | l cocktail bitters essence |
| 0.8 | l citric acid, 50% |
| 4 | l dye, 5%, dissolved in water |
| 102.4 | l |

| | | -continued |
|---|---|---|
| ./. | 2.4 | l contraction |
| | 100.0 | l final product |
| | | V - Wine-flavored Gumdrops |
| (1.) | 75.00 | g gelatine, 180° Bloom |
| | 5.00 | g agar |
| | 210.00 | g water |
| (2.) | 68.00 | g water |
| | 290.00 | kg granulated sugar |
| | 330 | g glucose syrup, 45° Baumé |
| | 10.00 | g glycerine |
| | 35.00 | g citric acid, 50% in water |
| | 12 | g dye solution, 5% in water |
| | 1035.00 | g |

Directions for Preparation

For 1.: Dissolve 5.0 g agar in 210.0 g water and boil briefly. Cool solution to 75° C. and add 75.0 g gelatine.

For 2.: Dissolve 290.0 g granulated sugar in 80.0 g water and boil.

Add 330.0 g glucose syrup and cook to 118° C.

Cool the boiled solution down to 70° C. Then add the gelatine-agar solution and 10.0 g glycerine.

When the wine-flavored gum mixture is at 65° C., the indicated quantities of acid and dye and flavoring as desired are mixed in.

EXEMPLARY REALIZATIONS

| VI - Shashlik sauce (tomato catsup) | |
|---|---|
| 8.0 | g citric acid |
| 10.0 | g mustard (medium-hot) |
| 25.0 | g table salt |
| 30.0 | g starch 3818 from the Maizena company |
| 100.0 | g vinegar, 10% |
| 100.0 | g Puritose (glucose syrup, Maizena brand) |
| 130.0 | g sugar |
| 8.5 | g dye solution (3% in water) |
| 588.5 | g water |
| 1000.0 | g |

The use of the dye according to the invention permits a saving of tomato paste. However, dye and tomato paste may be mixed in as desired.

| VII - Salad Dressing | |
|---|---|
| 1.0% | table salt |
| 1.5% | sugar |
| 2% | mustard |
| 5% | vinegar, 10% |
| 5.5% | Mayomil M (brand of Schmidt company) |
| 6% | egg yolk |
| 28.25% | water |
| 0.85% | dye (3% solution in water) |
| 50% | salad oil |
| 100% | |
| VIII - Fruit Preparation | |
| 0.4% | Frimulsion IQU |
| 30% | fruit |
| 42% | sugar |
| 12% | glucose syrup |
| 0.4% | sodium citrate |
| 15.2% | water |
| 100% | |

The fruit preparation produced in this manner is then dyed with the dye according to the invention in accordance with the intended use.

IX—Paper

In a 1% aqueous solution, preferably having a pH value of 4.5, the paper is dyed by being immersed once and then dried. This produces an intense red color. Changes in the color intensity can be effected by shifting the pH value.

A similar process can be carried out on textiles and leather.

I claim:

1. A natural, edible dye, in particular for coloring foodstuffs and snack foods, beverages, and pharmaceutical and cosmetic products, characterized by the infrared spectrum according to FIG. 1 and the ultraviolet spectrum according to FIG. 2.

2. A method for producing the dye as defined by claim 1, characterized in that the cells of the skins of colored beans of the genus Phaseolus are destroyed; the released dye is extracted with water or an aqueous solution of a weak organic acid following a weak acidulation; the resultant extract is separated from the skin residues and the solution is concentrated and dried.

3. A method as defined by claim 2, characterized in that the destruction of the cells is performed by means of treatment with a suitable enzyme.

4. A method as defined by claim 2, characterized in that the extraction is performed with the aqueous solution of a hydroxycarboxylic acid.

5. A method as defined by claim 4, characterized in that the extraction is performed with aqueous citric acid.

6. A method as defined by claim 2 or 3, characterized in that the bean skins, in order to prepare them for the cell destruction, are cooked with diluted, aqueous solutions of an organic acid and brought to the pH value and temperature suitable for enzymatic cell destruction.

7. A method as defined by claim 2 or 3, characterized in that further acid is added after the cell destruction and before the concentration steps.

8. A method as defined by claim 3, characterized in that acid amylase is used as the enzyme.

9. A method for producing the dye as defined by claim 1, characterized in that
 (a) the skins of colored soy beans or the powder thereof are boiled for some time with enough slightly acidic water that an easily stirrable suspension results, and the pH value after 10 to 15 minutes' boiling should be approximately 5 to 5.5;
 (b) after cooling to a temperature which is efficacious for the next method step below, the cell walls of the bean skins are at least partially destroyed by enzymatic decomposition, grinding at low temperatures or by autoclaving at elevated pressure and increased temperature in order to release the dye;
 (c) the obtained suspension is again brought to a pH value of approximately 4 to 4.5 by means of the addition of a weak organic acid;
 (d) the suspension obtained according to method step (c) is separated into skin residues and dye solution; and
 (e) the dye solution is concentrated until dry.

10. A method as defined by claim 2, characterized in that the dye is spray-dried.

11. A method of using the dye as defined by claim 1 for dyeing textiles, paper and leather.

* * * * *